United States Patent [19]

Murray

[11] Patent Number: 4,710,463
[45] Date of Patent: Dec. 1, 1987

[54] RECOMBINANT DNA MOLECULES CAPABLE OF EXPRESSING HBV CORE AND SURFACE ANTIGENS

[75] Inventor: Kenneth Murray, Heidelberg, Fed. Rep. of Germany

[73] Assignee: Biogen N.V., Curacao, Netherlands Antilles

[21] Appl. No.: 363,763

[22] Filed: Mar. 31, 1982

Related U.S. Application Data

[63] Continuation of Ser. No. 107,441, Dec. 26, 1979, abandoned.

[30] Foreign Application Priority Data

Dec. 22, 1978 [GB] United Kingdom ............... 49907/78
Dec. 27, 1978 [GB] United Kingdom ............... 50039/78
Nov. 1, 1979 [GB] United Kingdom ................. 7937910

[51] Int. Cl.$^4$ ..................... C12P 21/00; C12P 21/02; C12P 19/34; C12N 15/00; C12N 1/20; C12N 1/00; C07H 15/12; C07K 13/00

[52] U.S. Cl. ........................................ 435/68; 435/70; 435/91; 435/172.3; 435/253; 435/320; 536/27; 530/350; 530/806; 530/808; 514/12; 935/12

[58] Field of Search ................... 435/172, 317, 68, 70; 536/27; 935/4, 9, 12, 39, 44, 47

[56] References Cited

PUBLICATIONS

Landers et al., Journal of Virology, vol. 23, pp. 368-376, Aug. 1977.
Khorana et al., The Journal of Biological Chemistry, vol. 251, pp. 565-570 and 667-675, (1976).
Helling et al., Genetic Engineering, Edited by Chakrabarty, CRC Press Inc., pp. 1-30, (1978).
Fritsch et al., C. R. Academy of Sciences, Paris V. 287, pp. 1453-1456, Dec. 18, 1978.
Mercereau-Puijalon et al., Nature, vol. 275, pp. 505-510, Oct. 12, 1978.
Peterson et al., PNAS USA, vol. 74, pp. 1530-1534, Apr. 1977.
Summers et al., PNAS USA, vol. 72, pp. 4597-4601, Nov. 1975.
Fritsch et al., Translation C. R. Academy of Sciences Paris V. 287 Series D-1453, Dec. 18, 1978.
Burrell et al., Nature, vol. 279, pp. 43-48, May 3, 1979.
Valenzuela et al., Nature, vol. 280, pp. 815-819, Aug. 30, 1979.
Galibert et al., Nature, vol. 281, pp. 646-650, Oct. 25, 1979.
Villa-Komaroff et al., PNAS USA, vol. 75, pp. 3727-3731, Aug. 1978.
Goeddel et al., Nature, vol. 281, pp. 544-548, Oct. 18, 1979.
O'Farrell et al., J. of Bacteriology, vol. 134, pp. 645-654, May 1978.
Polislay et al., PNAS USA, vol. 73, pp. 3900-3904, Nov. 1976.

Primary Examiner—Alvin E. Tanenholtz
Attorney, Agent, or Firm—James F. Haley, Jr.; Margaret A. Pierri

[57] ABSTRACT

Recombinant DNA molecules and hosts transformed with them which produce polypeptides displaying HBV antigenicity and genes coding therefor and methods of making and using these molecules, hosts, genes and polypeptides. The recombinant DNA molecules of this invention are characterized by structural genes that code for at least one polypeptide displaying HBV antigenicity. In appropriate hosts these recombinant DNA molecules permit the production and identification of genes and polypeptides characteristic of HBV antigenicity and their use in compositions and methods for detecting HBV virus infections in humans and stimulating the production of antibodies against this infection.

36 Claims, 12 Drawing Figures

```
 1   GlyGlyLeuPheHisLeuCysLeuIleIleSerCysSerCysProThrValGlnAlaSerLysLeuCysLeuGlyTrpLeu***
 2                                                                               -20
 3   GGGGGCTTTTTCACCTCTGCCTAATCATCTCTTGTTCATGTCCTACTGTTCAAGCCTCCAAGCTGTGCCTTGGGTGGCTTTAGGGC
                    -80              -60              -40
                                                                                       AluI

1   MetAspIleAspProTyrLysGluPheGlyAlaThrValGluLeuLeuSerPheLeuProSerAspPhePheProSerValArgAsp
 2                       ***              ***                               ***
 3   ATGGACATTGACCCTTATAAAGAATTTGGAGCTACTGTGGAGTTACTCTCGTTTTTGCCTTCTGACTTCTTTCCTTCCGTACGAGAT
      1              20               40               60               80
       EcoRI* AluI

1   LeuLeuAspThrAlaAlaAlaLeuTyrArgAspAlaLeuGluSerProHisHisCysSerProGluHisThrAlaLeuArgGlnAla
 2                                        ***                                ***
 3   CTTCTAGATACCGCCGCAGCTCTGTATCGGGATGCCTTAGAGTCTCCTGAGCATTGTTCACCTCACCATACTGCACTCAGGCAAGCA
                  100              120              140              160

1   IleLeuCysTrpGlyAspLeuMetThrLeuAlaThrTrpValGlyThrAsnLeuGluAspProAlaSerArgAspLeuValValSer
 2         ***                    ******          ***              ***              ******
 3   ATTCTTTGCTGGGGAGACTTAATGACTCTAGCTACCTGGGTGGGTACTAATTTAGAAGATCCAGCATCTAGGGACCTAGTAGTCAGT
       180              200              220              240              260
                                              EcoRII                        AvaII

1   TyrValAsnThrAsnValGlyLeuLysPheArgGlnLeuLeuLeuTrpPheHisIleSerCysLeuThrPheGlyArgGluThrValLeu**
 2    ***                                                                  ***
 3   TATGTCAACACTAATGTGGGCCTAAAGTTCAGACAATTATTGTGGTTCCACATTTCTTGTCTCACTTTTGGAAGAGAAACGGTTCTA
                   280              300              320              340
                  HaeIII
```

FIG. 3

```
GluTyrLeuValSerPheGlyValTrpIleArgThrProProAlaTyrArgProProAsnAlaProIleLeuSerThrLeuProGlu
                                                  ***
         360                380                400                420
GAGTATTTGGTGTCTTTTGGAGTGTGGATTCGCACTCCTCCAGCTTATAGACCACCAAATGCCCTATCCTATCAACGCTTCCGGAG

ThrThrValValArgArgArgGlyArgArgArgThrProSerProArgArgArgArgSerGlnSerProArgArgArgArg
                                    ***                                        520
         440                460                480                500
ACTACTGTTGTTAGACGACGAGGCAGGTCCCCTAGAAGAAGAACTCCCTGCCTCGCAGAGACGAAGATCTCAATCGCCGGTCGCAGA
                          Ava1
ArgSerGlnSerArgGluSerGlnCys***
                                                                      600
         540                560                580                EcoRI*
AGATCTCAATCTCGGAATCTCAATGTTAGTATCCCTTGGACTCATAAGGTGGGAAATTTACTGGGCTTTATTCTTCTACTGTACC

***
         620                640                660                680
TGTCTTTAACCCTCATTGGAAACCGCCCCTCTTTTCCTAATATACATTTACACCAAGATATTATCAAAAAATGTGAACAGTTGTAGG

***             ***   ***
         700                720                740                760                780
GCGGCTCACAGTCAATGAGAAAAGAGGTTGAAATTGATCATGCCTGCTAGGTTTTATCCTAATTTTACCAAATATTTGCCCTTGGA
```

```
                                                                              860
                                             820                840
        800
TAAGGGTATTAAACCTTATTATTCCAGAACATCTAGTTAATCATTACTTCCAAACTAGACACTATTACACACTCTATGGAAGGCGGG 940
                                             900                920
        880                                   HaeII
TGTTTTATATAAGAGAGTATCAACACATAGCGCCTCATTTTGTGGGTCACCATATTCTTGGGAACAAGAGCTACAGCATGGGGCAGA
                                              HhaI                             AluI 1040
                                             980                1000   1020
        960
ATCTTTCCACCAGCAATCCCTCTGGGATTCTTTCCCGACCACCAGTTGGATCCAGCCTTCAGAGCAAACACCAACAATCCAGATTGGG 1120
                                             1060               1080   1100
                                                                               AluI
ACTTCAATCCCAACAAGGACACCTGGCCAGACGCCAACAAGGTAGGAGCTGGAGCATTCGGGCTAGGGTTCACCCGACCGGCACGGAG 1200
                                             1140               1160   1180
GCCTTTTGGGGTGGAGCCCTCAGGCTCAGGGCATAATGCAAACCTTGCCAGCAAATCCGCCTCCTGCCTCTACCAATCGCCAGTCAG
```

```
                                                                                    1280                                    1300
     1220              1240                    1260
1 GACGGGCAGCCTACCCCGTGTCTCCACCTCTGAGAACCACTCATCCTCAGGCCATGCACTGGAACTCCACAACCTTCCACCAAACTC
2
3                                     ***

1320                    1340                 1360                       1380
1 TGCAAGATCCCAGAGTGAGAGGCCTGTATTTCCCTGCTGGTGGCTCCAGTTCAGGGACACAGTAAACCCTGTTCCGACTACTACCTCTC
2
3                                                           ***

MetGluAsnIleThrSerGlyPheLeuLeuValLeu
                      1400             1420                        1440                     1460               1480
1 CCATATCGTCAATCTTCTCGAGGATTGGGGACCCTGCGCTGAACATGGAGAACATCACATCAGGATTCCTAGGACCCCTGCTCGTGTTA
2                        XhoI,AvaI                 HhaI
3                        TaqI
                                                               ***

GlnAlaGlyPhePheLeuLeuThrArgIleLeuThrIleProGlnSerLeuAspSerTrpTrpThrSerLeuAsnPheLeuGlyGly
                                    1500                    1520                      1540                 1560
1 CAGGCGGGGTTTTTCTTGTTGACAAGAATCCTCACATACCGAGAGTCTAGACTCGTGGTGGACTTCTCTCAATTTTCTAGGGGGA
2
3                                                   ***

ThrThrValCysLeuGlyGlnAsnSerGlnSerProIleSerAsnHisSerProThrSerCysProProThrCysProGlyTyrArg
                          1580                      1600                          1620                       1640
1 ACTACCGTGTGTCTTGGCCAAAATTCGCCAGTCCCCAATCTCCAATCACTCCAATCTCCAATCACTCCAACTTGTCCTGGTTATCGC
2                                                               EcoRI*
3
```

FIG. 6

```
    TrpMetCysLeuArgArgPheIleIlePheLeuPheIleLeuLeuCysLeuIleIlePheLeuLeuAspTyrGlnGly
                 1660                1680               1700              1720            1740
1
2   TGGATGTGTCTGCGGCGTTTATCATCTTCCTCTTCATCCTGCTGCTATGCCTCATCTTCTTGTTGGTTCTTCTGGACTATCAAGGT
3                                      ***

MetLeuProValCysProLeuIleProGlySerSerThrThrSerThrThrGlySerCysArgThrCysThrThrProAlaGlnGlyIle
                 1760                1780              1800              1820
1
2   ATGTTGCCCGTTTGTCCTCTAATTCCAGGATCATCAACCACCAGCACGGGATCCTGCAGAACCTGCACGACTCCTGCTCAAGGAATC
3                                                                          ___
                                                                           Pst

SerMetTyrProSerCysCysThrLysProSerAspGlyAsnCysThrCysIleProIleProSerSerTrpAlaPheGlyLys
               1840               1860               1880              1900
1
2   TCTATGTATCCCTCCTGTTGCTGTACAAAACCTTCGGATGGAAACTGCACCTGTATTCCCATCCCATCATCCTGGGCTTTCGGAAAA
3                                                            ***

PheLeuTrpGluTrpAlaSerAlaArgPheSerTrpLeuSerLeuLeuValProPheValGlnTrpPheValGlyLeuSerProIle
               1920               1940              1960              1980               2000
1
2   TTCCTATGGGAGTGGGCCCTCAGCCCGTTTCTCTTGGCTCAGTTTACTAGTGCCATTGTTCAGTGGTTCGTAGGGCTTTCCCCCATT
3                                                     ***

ValTrpLeuSerValIleTrpMetMetTrpTyrTrpGlyProSerLeuTyrSerIleLeuSerProPheLeuProLeuProIle
               2020              2040              2060              2080
1
2   GTTTGGCTTTCAGTTATATGGATGATGTGGTATTGGGGGCCAAGTCTGTACAGCATCTTGAGTCCCTTTTTACCGGCTGTTACCAATT
3                                       ***
```

```
          ***
      PhePheCysLeuTrpAlaTyrIle***
         2100                2120                2140                2160
1 TTCTTTTGTCTCTTGGGCATACATTTAAACCCTAACAAAACAAAAGATGGGGTTATTCTCTAAATTTCATGGGCTATGTCATTGGAT
2
3

2180                2200                2220                2240                2260
1 GTTGGGGATCATTGCCACAAGATCACATCATACACAAAATCAAAGAATGTTTAGAAAACTCCCTGTTCACAGGCCTATTGATTGGA
2
3

***                 2340
       2280                2300                2320
1 AAGTGTGTCAACGAATTGTGGGTCTTCTCTGGGTTTGCTGCCCCTTTCACACACAATGTGGTTATCCTGCTTAATGCCCTTGTATGCAT
2
3

***                                         ***
       2360                2380                2400                2420
1 GTATTCAATCTAAGCAGGCTTTCACTTTTTCGCCAACTTACAGGCCTTTCTGTGTAAACAATACCTGAACCTTTACCCCGTTGCCG
2
3

2520
       2440                2460                2480                2500
1 AGCAACGGGCCAGGTCTGTGCCAAGTGTTTGCTGATGCAACCCCCACTGGGCTTGGTCATGGGCCATCAGCGGCATGGTGTGGAA
2
3
```

```
           2540                2560           ***      2580                    2600
1  CCTTTCTGGCTCCTCCTGCCGATCCATACTGCGGAACTCCTAGCCGCTTGTTTTGCTCGCAGCAGGTCTGGAGCAAACATTCTCGGAA
2
3

***       2620                  2640
1  CTGACAACTCTGTTGTCCTCTCCCGCAAATATACATCGTTTCCA
2
3
```

FIG. 9

RECOMBINANT DNA MOLECULES CAPABLE OF EXPRESSING HBV CORE AND SURFACE ANTIGENS

This is a continuation of application Ser. No. 107,441, filed Dec. 26, 1979 and now abandoned.

TECHNICAL FIELD OF INVENTION

This invention relates to recombinant DNA molecules and their method of production. This invention relates more particularly to recombinant DNA molecules expressed in appropriate host organisms. The recombinant DNA molecules disclosed herein are characterized by the DNA that codes for polypeptides with the specificity of hepatitis B viral antigens. As will be appreciated from the disclosure to follow, the recombinant DNA molecules may be used in the detection of hepatitis B virus in man and the stimulation of antibodies in humans against this virus.

BACKGROUND ART

The virus that causes hepatitis B or serum hepatitis appears to infect only man. Hepatitis B virus ("HBV") infection in humans is widespread. In the United Kingdom, United States, and Western Europe, approximately 0.1% of all blood donors are chronic carriers of HBV. While the death rate due to viral hepatitis is not high (in 1975 in the United Kingdom it was 3 per million), there are indications that as many as 5% of the population in the United Kingdom and 15% of the population in the United States have been infected. In many African and Asian countries, up to twenty percent of the population are chronic carriers of HBV, and over fifty percent of all adults in those countries have been or are infected with HBV.

The hepatitis infection is transmitted by three general mechanisms: (1) by parenteral inoculation of infected blood or body fluids, either in large amounts as in blood transfusions or in minute amounts as through an accidental skinprick; (2) by close family or sexual contact; and (3) by some mothers, who infected during pregnancy, transmit the virus to their new-born children. Under natural conditions, HBV is not highly contagious. Transmission by inhalation occurs rarely, if ever.

Most HBV infections are subclinical. The clinical illness usually lasts three to six weeks and ranges in severity from mild to acute fulminating hepatitis followed by cirrhosis or death. Recovery from clinical and subclinical HBV infections is usually complete. However, serious long term consequences result in some cases: (1) approximately five percent of acute infections lead to chronic carriage of hepatitis B virus antigen with its continuing potential for infectivity to others and ongoing liver damage; and (2) it is likely that past infection with HBV may be wholly or partly responsible for the initiation of a significant proportion of HBV-seronegative cases of chronic active hepatitis, cirrhosis and primary liver carcinoma.

Recent advances in molecular biology have made it possible to introduce the DNA coding for specific non-bacterial eukaryotic proteins into bacterial cells. In general, with DNA other than that prepared via chemical synthesis, the construction of the recombinant DNA molecules comprises the steps of producing a single-stranded DNA copy (cDNA) or a purified messenger (mRNA) template for the desired protein; converting the cDNA to double-stranded DNA; linking the DNA to an appropriate site in an appropriate cloning vehicle and transforming an appropriate host with that recombinant DNA molecule. Such transformation permits the host to produce the desired protein. In addition, at least in the case of ovalbumin DNA, it is known that appropriate fusion of the particular DNA to a strong bacterial promoter or expression control sequence produces larger amounts of the desired ovalbumin protein, i.e., about 0.5 to 1% of the total protein mass of an *E. coli* cell (O. Mercereau-Puijalon et al., "Synthesis Of An Ovalbumin-Like Protein By *Escherichia coli* K12 Harboring A Recombinant Plasmid", Nature, 275, pp. 505–510 (1978) and T. H. Fraser and B. J. Bruce, "Chicken Ovalbumin Is Synthesized And Secreted By *Escherichia coli*", Proc. Natl. Acad. Sci. USA, 75, pp. 5936–5940 (1978)).

Several non-bacterial proteins and genes have been synthesized using recombinant DNA technology. These include a protein displaying rat proinsulin antigenic determinants (L. Villa-Komaroff et al., "A Bacterial Clone Synthesizing Proinsulin", Proc. Natl. Acad. Sci. USA, 75, pp. 3727–3731 (1978)), rat growth hormone (P. H. Seeburg et al., "Synthesis Of Growth Hormone By Bacteria", Nature, 276, pp. 795–798 (1978)), mouse dihydrofolate reductase (A. C. Y. Chang et al., "Phenotypic Expression in *E. coli* Of A DNA Sequence Coding For Mouse Dihydrofolate Reductase", Nature, 275, pp. 617–624 (1978)), somatostatin (K. Itakura et al., "Expression In *Escherichia coli* Of A Chemically Synthesized Gene For The Hormone Somatostatin", Science, 198, 1056–1063 (1977), United Kingdom Pat. specification Nos. 2,007,675A, 2,007,676A and 2,008,123A and cognate applications in other countries), and the A and B polypeptide chains of human insulin (D. V. Goeddel et al., "Expression In *Escherichia coli* Of Chemically Synthesized Genes For Human Insulin", Proc. Natl. Acad. Sci. USA, 76, pp. 106–110 (1979) and the United Kingdom and related patent specifications, supra).

None of the foregoing, however, is directed, as is this invention, toward the recombinant DNA synthesis of viral proteins such as hepatitis B virus antigens.

It is known that HBV infections cause development of antibodies to the antigens of the virus. These antibodies are the body's defense mechanism to the HBV infection. The development of such antibodies prior to exposure or rapidly in the case of potential exposure should substantially reduce and combat virus growth and spread in the patient.

A problem however in the artifically stimulated development of antibodies to the antigens of hepatitis B virus is the limited host range of the virus. For example, although highly infectious to man, experimental infection with hepatitis B virus has been achieved in only a few additional primates. And, the virus has not been propagated in tissue culture. This limited host range and inability to infect tissue culture cells has severely hampered both the characterization of the virus and the pathology of its infection and the development of rapid detection means and effective means of infection control and prevention.

While there have been some attempts to employ authentic HBV viral antigens, isolated from victims of the HBV infection, for the development of antibodies and detection of infection, these treatments are not generally available because of the limited supply of the active species. Furthermore, the use of human sources for these antigens is disfavored because of the well recognized contamination problems in using human isolates.

DISCLOSURE OF THE INVENTION

The present invention solves the problems referred to by providing in accordance with the invention a recombinant DNA molecule characterized by a structural gene coding for a polypeptide displaying HBV antigenicity.

By virtue of our invention, it is possible to obtain HBV antigens and genes in substantial and uncontaminated quantities for vaccine preparations and for use in detection of the viral infection and determination of its pathology and molecular biology. Such supplies have not hitherto been available, because of the narrow host range of the virus and its inability to be grown in tissue culture.

As will be appreciated from the disclosure to follow, the recombinant DNA molecule of the invention is capable of producing, in an appropriate host, at least one viral polypeptide displaying HBV antigenicity and the structural genes that code therefor. These recombinant DNA molecules and hosts may be utilized to prepare polypeptides displaying HBV antigenicity and structural genes coding for these polypeptides. These products may also be identified and characterized and are useful either as produced in the host or after appropriate derivatization or modification in compositions and methods for improving production of these products themselves and for detecting HBV infection, tracing its pathology and stimulating the production of HBV antibodies in humans.

In accordance with the invention we also provide a process for producing a recombinant DNA molecule, characterized by linking a DNA sequence prepared from the endogenous DNA of a Dane particle to another DNA sequence prepared from a source other than the Dane particle.

Our process may be distinguished from the prior processes above mentioned in that none of the prior processes employs a natural gene or DNA for a particular protein for construction of the recombinant DNA molecule and production of that protein or gene. Instead, they employ either synthetic genes made by chemical synthesis or artificial genes made by enzymatically copying the mRNA isolated from the donor cell to poduce cDNA sequences.

One reason that natural DNA has not been previously employed directly in recombinant DNA synthesis of proteins in that natural DNA's from most higher organisms and at least some animal viruses contain "introns" or additional nucleotide sequences as part of the gene. These introns do not form part of the final message of the gene. Instead, they are removed in vivo in higher organisms by special processing enzymes acting upon the primary transcription product to afford the ultimate message (mRNA) of the gene. Bacteria are presumed to be unable to process such introns so that natural DNA would not be expected to be expressed in bacterial hosts and the desired proteins would not be expected to be produced by these hosts.

BRIEF DESCRIPTION OF THE DRAWINGS

FIGS. 3–9 show the nucleotide sequence determined for a part of a hepatitis B virus genome in accordance with this invention. The sequence is displayed with the stop codons in the three reading frames noted above it. It is arbitrarily numbered from the initiation codon for the gene coding for HBcAg as determined in this invention. Nucleotides −80 to −1 represent a leader sequence which precedes this gene. Nucleotides 1–549 represent the nucleotide sequence for the gene coding for hepatitis B virus core antigen, the amino acid sequence (reading frame 1) of this antigen being depicted above that sequence. Nucleotides 1437–2114 represent the nucleotide sequence determined for the gene of hepatitis B virus surface antigen, the amino acid sequence (reading frame 3) of this antigen being depicted above that sequence. Various restriction endonuclease recognition sites in these genes are also depicted in FIGS. 3–9.

BEST MODE OF CARRYING OUT THE INVENTION

Figure 1:
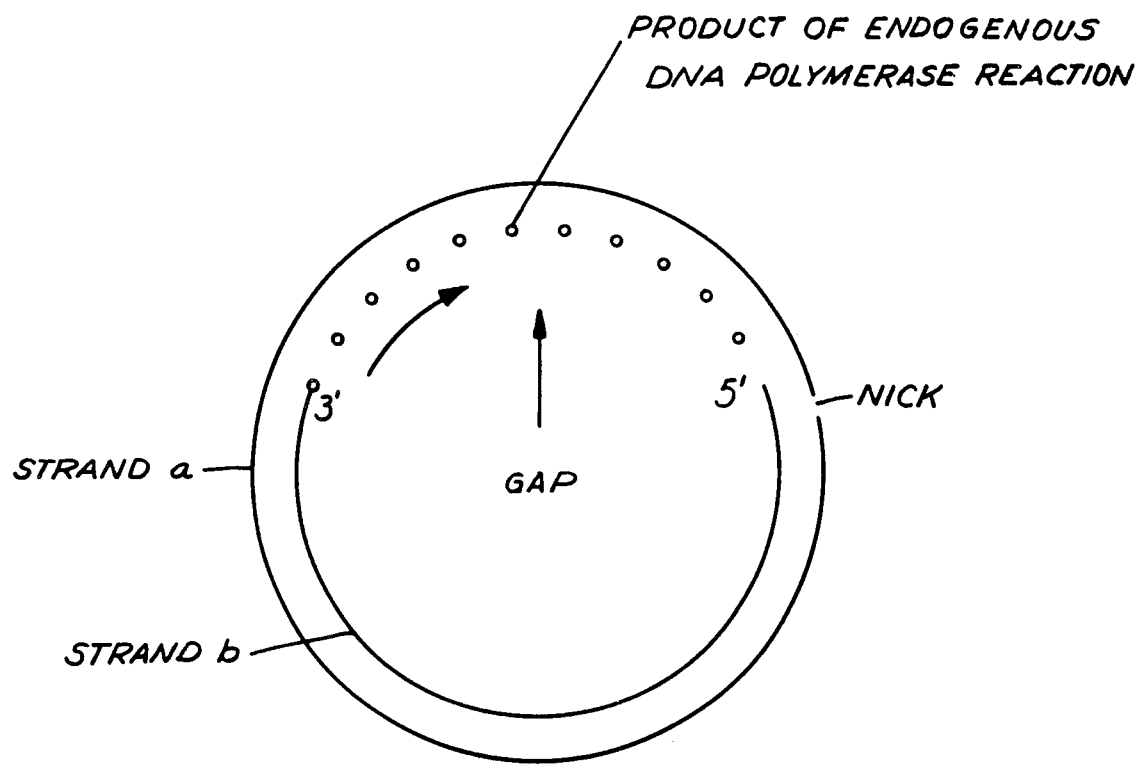
FIG. 1 is a simplified diagram representing the structure of the endogenous DNA of a Dane particle. It displays the two complementary DNA strands, strand a and b, the nick in strand a and the gap in strand b and the closing of that gap by DNA polymerase reaction.

In order that the invention herein described may be more fully understood, the following detailed description is set forth.

In the description the following terms are employed:

Nucleotide

A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U"). A and G are purines, abbreviated to R, and C, T, and U are pyrimidines, abbreviated to Y.

DNA Sequence

A linear series of nucleotides connected one to the other by phosphodiester bonds between the 3' and 5' carbons of adjacent pentoses.

Codon

A DNA sequence of three nucleotides (a triplet) which encodes through mRNA an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.

Reading Frame

The grouping of codon's during translation of mRNA into amino acid sequences. During translation the proper reading frame must be maintained. For example, the sequence GCTGGTTGTAAG may be translated in three reading frames or phases, each of which affords a different amino acid sequence:

GCT GGT TGT AAG—Ala-Gly-Cys-Lys
G CTG GTT GTA AG—Leu-Val-Val
GC TGG TTG TAA A—Trp-Leu-(STOP)

Polypeptide

A linear series of amino acids connected one to the other by peptide bonds between the α-amino and carboxy groups of adjacent amino acids.

Genome

The entire DNA of a substance. It includes inter alia the structural genes encoding for the polypeptides of the substance, as well as operator, promotor and ribosome binding and interaction sequences including sequences such as the Shine-Dalgarno sequences.

Structural Gene

A DNA sequence which encodes through its template or messenger RNA ("mRNA") a sequence of amino acids characteristic of a specific polypeptide.

Transcription

The process of producing mRNA from a structural gene.

Translation

The process of producing a polypeptide from mRNA.

Expression

The process undergone by a structural gene to produce a polypeptide. It is a combination of transcription and translation.

Plasmid

A non-chromosomal double-stranded DNA sequence comprising an intact "replicon" such that the plasmid is replicated in a host cell. When the plasmid is placed within a unicellular organism, the characteristics of that organism are changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage

Bacterial virus many of which include DNA sequences encapsidated in a protein envelope or coat ("capsid"). In a unicellular organism a phage may be introduced as free DNA by a process called transfection.

Cloning Vehicle

A plasmid, phage DNA or other DNA sequences which are able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning

The selection and propagation of a single species

Recombinant DNA Molecule

A hybrid DNA sequence comprising at least two nucleotide sequences, the first sequence not normally being found together in nature with the second.

Expression Control Sequence

A DNA sequence of nucleotides that controls and regulates expression of structural genes when operatively linked to those genes.

Referring now to FIG. 1, we have shown therein a simplified diagram of the endogenous DNA of a Dane particle. Dane particles are detectable in the blood plasma of some patients with hepatitis B viral infections (D. S. Dane and C. H. Cameron, "Virus-Like Particles In Serum Of Patients With Australia-Antigen Associated Hepatitis", The Lancet, 1, pp. 695–698 (1970)). This particle is thought to be identical or closely related to the infective virion of hepatitis B. While its size is known (42 nanometers in diameter), its structure is not fully understood. Generally, the Dane particle is believed to consist of an outer layer and an inner core. The outer layer of the particle generally contains a polypeptide known as hepatitis B surface antigen ("HBsAg"). The inner core (27 nanometers in diameter) contains a second polypeptide, hepatitis B core antigen ("HBcAg"), as well as an endogenous double-stranded, circular, DNA molecule of $2.1 \times 10^6$ daltons, which contains a single-stranded gap of varying length. A third polypeptide, 'e' antigen ("HBeAg"), may also be associated with the Dane particles. In addition, the Dane particle is believed to include an endogenous DNA dependent DNA polymerase that partially closes the single-stranded gap in the endogenous DNA by polymerase reaction employing that DNA as a primer/template. The structure and properties of the Dane particle and more especially its DNA have been the subject of several analyses. E.g., W. S. Robinson, "The Genome of Hepatitis B Virus", Ann. Rev. Microbiol., 31, pp. 357–377 (1977). However, the actual structure of the various antigens or their genes had not been determined.

The Dane particle's endogenous DNA has been isolated by extraction from the Dane particle. It consists of one nucleotide strand of constant length having a small nick or opening in it (FIG. 1, strand a, ~3000 nucleotides) and a second nucleotide strand of somewhat variable length (FIG. 1, strand b, ~2000 nucleotides). The second strand is complementary with the first and overlaps its nick to complete a circular structure by hydrogen bonding between complementary bases in the standard Watson-Crick manner. This overlap is apparent from FIG. 1. The DNA polymerase of the Dane particle appears to use the second strand of the endogenous DNA as a primer and the first strand as a template to fill in the variable gap with nucleotides which are complementary to the nucleotides of the first strand and afford a double-stranded DNA of about 3000 nucleotide pairs.

A METHOD OF PREPARATION OF HEPATITIS B VIRUS DNA

Human serum from a single HBsAg positive, HBeAg positive donor (serotype adyw) was diluted with an equal volume of buffer (0.1M tris-HCl, 0.1M saline (NaCl), 0.1% (weight/volume as used throughout)2-mercaptoethanol, 0.1% bovine serum albumin, 0.001M EDTA) at pH 7.4. This was centrifuged at 35,000 r.p.m. for 2 hours at 4° C. The pellet thus obtained was resuspended in 200 μl of the same buffer and layered at the top of a centrifuge tube containing 20% sucrose. The suspension was centrifuged at 40,000 r.p.m. for 2 hours at 4° C. The pellet thus obtained was again resuspended in 100 μl of buffer (0.1M tris-HCl, 0.1M saline) at pH 7.5.

The resultant DNA containing-pellet was then labelled with $^3H$ or $^{32}P$ as described by P. M. Kaplan et al., "DNA Polymerase Associated With Human Hepatitis B Antigen", *J. Virol.*, 12, pp. 995-1005 (1973) to facilitate tracing it through subsequent steps of the process. This labelling results from the reaction of the concentrated Dane particles and $^3H$-or $^{32}P$-labelled deoxynucleoside triphosphates (dNTP's) for 4 hours at 37° C. After this DNA polymerase reaction, which results in partially closing the single-stranded gap in the DNA (See FIG. 1), the labelled DNA material was layered at the top of a centrifuge tube containing 30% sucrose and centrifuged at 42,000 r.p.m. for 3½ hours at 4° C.

Figure 2:
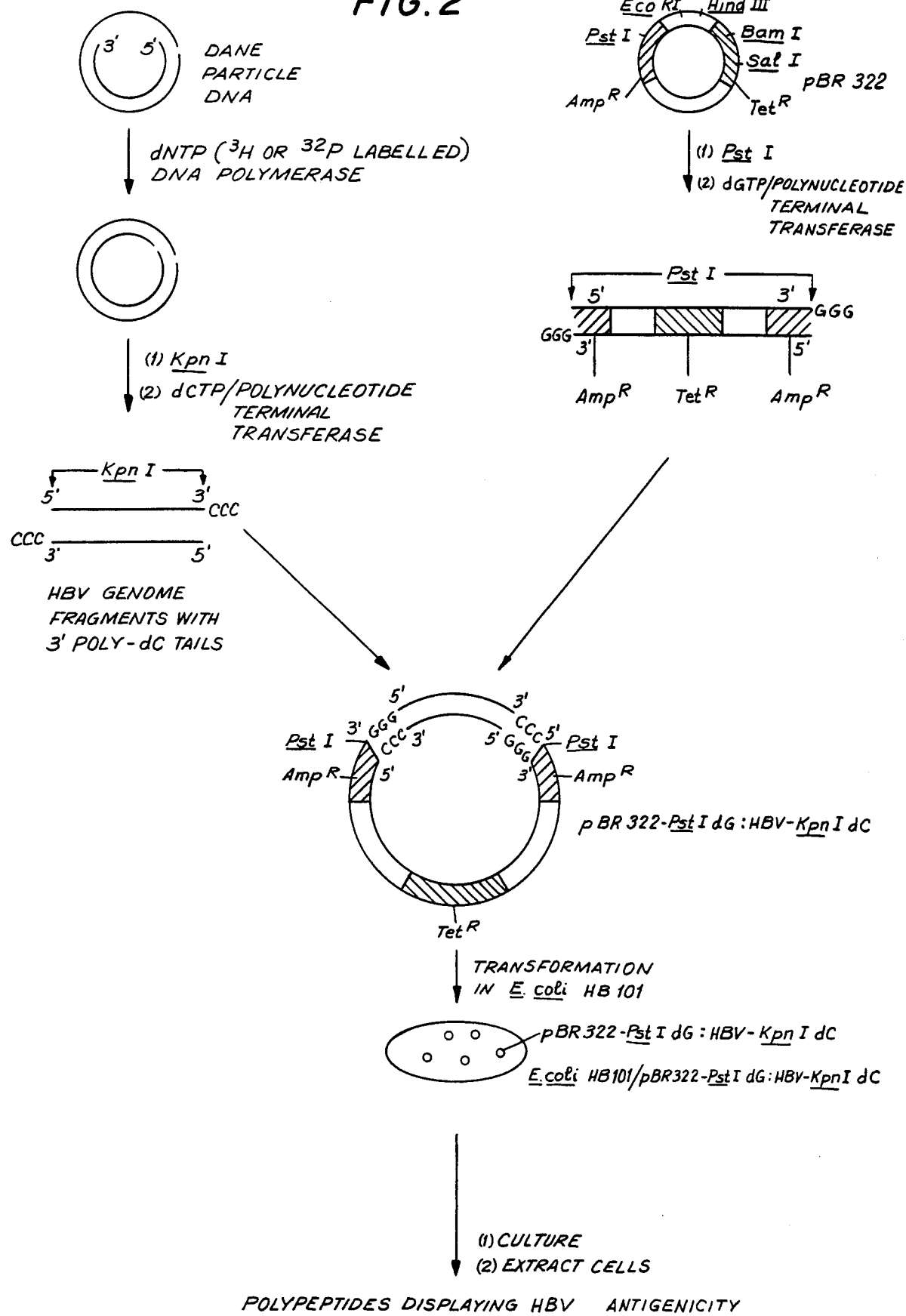
FIG. 2 is a schematic outline of the preferred embodiment of the process of this invention: fragments of the endogenous DNA isolated from the Dane particle are fused to the E. coli penicillinase gene on the plasmid pBR322 at the Pst I site. After transformation into E. coli HB101, the recombinant DNA molecule pBR322-Pst I dG: HBV-KpnI dC directs the synthesis of polypeptides displaying HBV antigenicity.

The DNA was then extracted with phenol from the resulting pellet using the procedure of L. I. Lutwick and W. S. Robinson, "DNA Synthesized In The Hepatitis B Dane Particle DNA Polymerase Reaction", *J. Virol.*, 21, pp. 96-104 (1977). The extracted DNA was then dialyzed against a solution of 0.01M tris-HCl, 0.001M EDTA (pH 8.0) to eliminate the phenol solvent. The isolated DNA was then ready for restriction enzyme digestions. It displayed a specific radioactivity of $\sim 10^8$ cpm/μg. The above discussed process is schematically depicted in FIG. 2.

CLONING OF HEPATITIS B VIRUS DNA

A wide variety of host-cloning vehicle combinations may be usefully employed in cloning the double-stranded DNA isolated as above. For example, useful cloning vehicles may include chromosomal, non-chromosomal and synthetic DNA sequences such as various known bacterial plasmids such as pBR322, other *E. coli* plasmids and their derivatives and wider host range plasmids such as RP4, phage DNA such as the numerous derivatives of phage λ, e.g., NB989 and vectors derived from combinations of plasmids and phage DNA's such as plasmids which have been modified to employ phage DNA expression control sequences. Useful hosts may include bacterial hosts such as *E. coli* X1776, *E. coli*, X2282, *E. coli* HB101 and *E. coli* MRC1 and strains of Pseudomonas, *Bacillus subtilis* and other bacilli, yeasts and other fungi, animal or plant hosts such as animal or plant cells in culture and other hosts. Of course, not all hosts may be equally efficient. The particular selection of host-cloning vehicle combination may be made by those of skill in the art after due consideration of the principles set forth above without departing from the scope of this invention.

Figure 11:
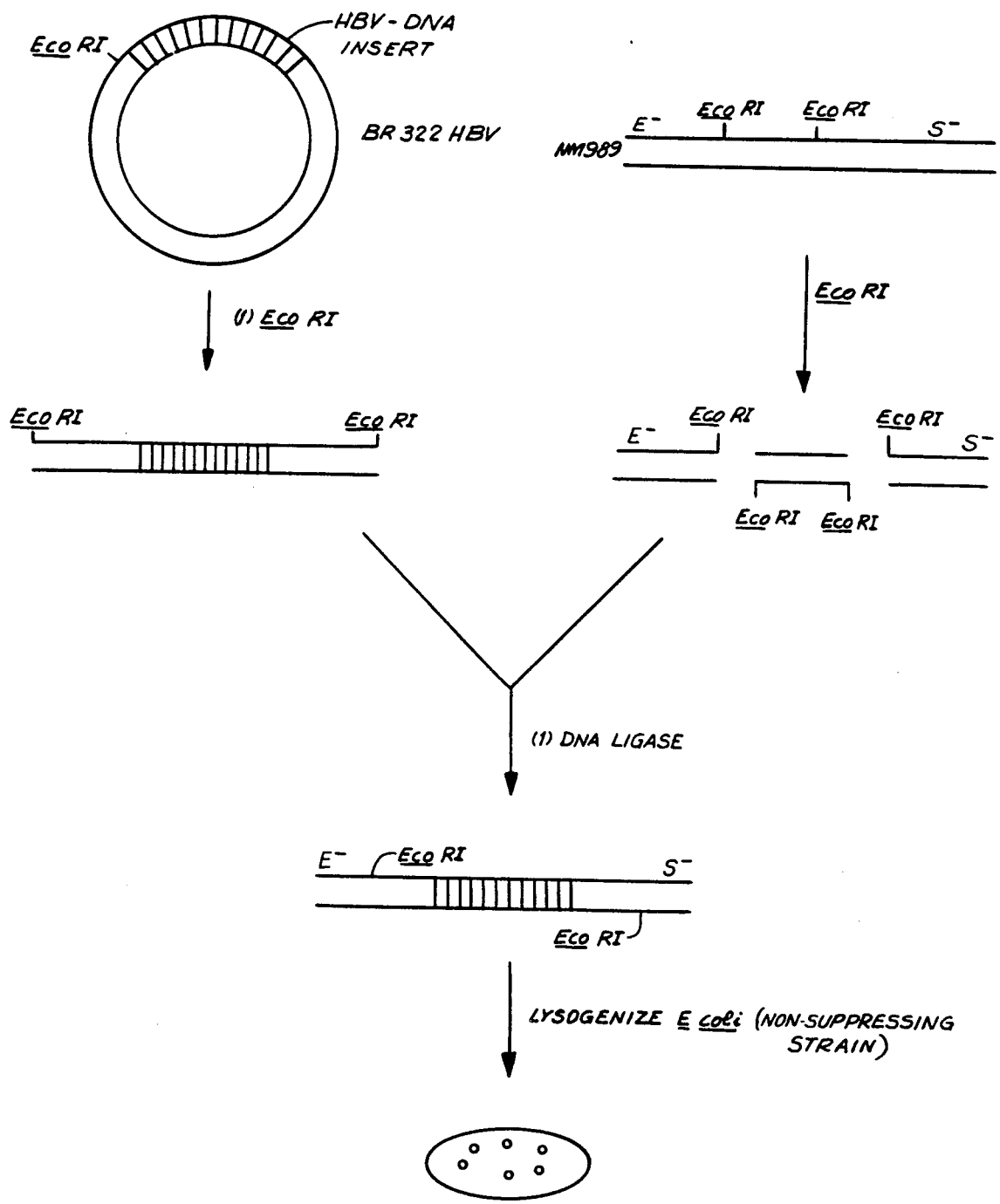
FIG. 11 is a schematic outline of a process of this invention wherein a recombinant DNA molecule of this invention is fragmented and connected to a fragment of phage DNA for use in lysogenizing host cells and thereby increasing the number of gene copies therein.
Figure 12:
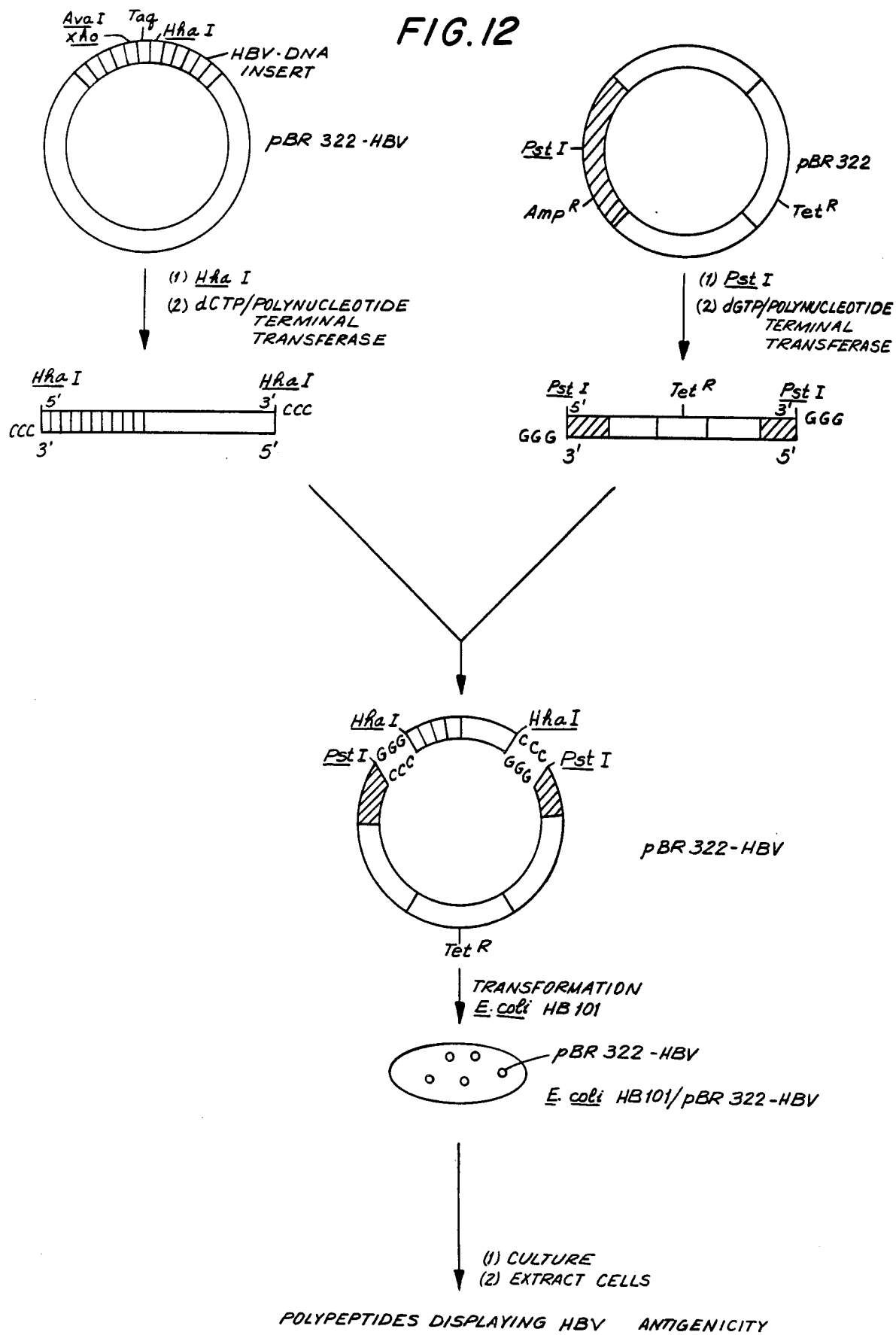
FIG. 12 is a schematic outline of another embodiment of the process of this invention: a recombinant DNA molecule of this invention which does not produce a polypeptide displaying hepatitis B virus core antigenicity is fragmented to remove the structural gene for HBsAg and this structural gene employed to produce a recombinant DNA molecule which produces HBsAg in an appropriate host.

Furthermore, within each specific vector, various sites may be selected for insertion of the isolated double-stranded DNA. These sites are usually designated by the restriction enzyme or endonuclease that cuts them. For example, in pBR322 the Pst I site is located in the gene for penicillinase between the nucleotide triplets that code for amino acids 181 and 182 of the penicillinase protein. This site was employed by Villa-Komaroff et al., supra, in their synthesis of protein displaying rat proinsulin antigenic determinants. A Hind II endonuclease recognition site is between the triplets coding for amino acids 101 and 102 and a Taq site at the triplet coding for amino acid 45 of that protein in pBR322. In similar fashion, the Eco RI endonuclease recognition site for this plasmid is located between the genes coding for resistance to tetracycline and ampicillin, respectively. This site was employed by Itakura et al. and Goeddel et al. in their recombinant DNA synthetic schemes, supra. FIGS. 2 and 11 display for illustrative purposes some of the restriction sites in plasmid pBR322 and phage λ NM989.

The particulr site chosen for insertion of the selected DNA fragment into the cloning vehicle to form a recombinant DNA molecule is determined by a variety of factors. These include size and structure of the polypeptide to be expressed, susceptibility of the desired polypeptide to endoenzymatic degradation by the host cell components and contamination by its proteins, expression characteristics such as the location of start and stop codons, and other factors recognized by those of skill in the art. Since the expression process is not fully understood, none of these factors alone absolutely controls the choice of insertion site for a particular polypeptide. Rather the site chosen effects a balance of these factors and not all sites may be equally effective for a given protein.

Although several methods are known in the art for inserting foreign DNA into a cloning vehicle to form a recombinant DNA molecule, the method preferred in accordance with this invention is displayed in FIG. 2. It is characterized by cleaving the Dane particle DNA with a restriction endonuclease, attaching poly-deoxyC sequences to the 3' termini (named by convention from the deoxyribose carbon of the DNA sugar backbone) of the cleaved DNA and linking the elongated DNA to a cloning vehicle which has been cut at a particular site by a restriction endonuclease and elongated at the 3' termini of that cut with poly deoxyG sequences, that are complementary to the poly-dC sequences of the cleaved DNA. The complementary character of the 3' tails of the DNA and cloning vehicle permit cohesion of those termini.

To be useful in the process of this invention a restriction enzyme chosen to cleave the HBV DNA should not cleave the HBV DNA within an essential part of the gene that codes for polypeptides displaying HBV antigenicity, and most suitably it should cleave the DNA at a limited number of sites. Restriction enzymes that have been employed in this invention include Kpn I, Bgl II, Bam HI, Ava I and Eco RI. Other restriction endonucleases may be similarly useful in accordance with this invention. Their selection may be made by those of skill in the art on due consideration of the factors set out above without departing from the scope of this invention. FIGS. 3-9 display some of the restriction endonuclease recognition sites in part of the HBV genome.

Of course, other known methods of inverting DNA sequences into cloning vehicles to form recombinant DNA molecules are equally useful in this invention. These include, for example, direct ligation wherein the same restriction endonuclease is employed to cleave the HBV DNA and the cloning vehicle. This procedure inherently provides complementary ends for cohesion.

It should, of course, be understood that the nucleotide sequence or gene fragment inserted at the selected restriction site of the cloning vehicle may include nucleotides which are not part of the actual structural gene for the desired protein or may include only a fragment of that structural gene. It is only required that whatever DNA sequence is inserted, the transformed host will produce a polypeptide displaying HBV antigenicity.

The recombinant DNA molecule containing the hybrid gene may be employed to transform a host so as to permit that host (transformant) to express the structural gene or fragment thereof and to produce the polypeptide or portion thereof for which the hybrid DNA codes. The recombinant DNA molecule may also be employed to transform a host so as to permit that host on replication to produce additional recombinant DNA molecules as a source of HBV structural genes and fragments thereof. The selection of an appropriate host for either of these uses is controlled by a number of factors recognized by the art. These include, for example, compatibility with the chosen vector, toxicity of the co-products, ease of recovery of the desired polypeptide, expression characteristics, biosafety and costs. Again, since the mechanisms of expression are not fully understood, no absolute choice of host may be made for a particular recombinant DNA molecule or polypeptide from any of these factors alone. Instead, a balance of these factors must be struck with the realization that not all hosts may be equally effective for expression of a particular recombinant DNA molecule.

In the present synthesis, the preferred cloning vehicle is the bacterial plasmid pBR322 and the preferred restriction endonuclease site therein is the Pst I site (FIG. 2). This plasmid is a small (molecular weight approx. 2.6 megadaltons) plasmid carrying resistance genes to the antibiotics ampicillin (Amp) and tetracycline (Tet). The plasmid has been fully characterized (F. Bolivar et al., "Construction and Characterization of New Cloning Vehicles II. A Multipurpose Cloning System", *Gene,* pp. 95–113 (1977)). The preferred host in accordance with this invention is *E. coli* HB101.

1. Preparation of dC-elongated Dane particle DNA

In actual practice of the preferred embodiment of this invention, the DNA isolated as above from the Dane particles was digested with restriction endonuclease Kpn I (approximately 20 ng DNA in 10 μl 10 mM tris-HCl, pH 7.5, 10 mM $MgCl_2$, 10 mM 2-mercaptoethanol, 40 mM NaCl, 0.5 μl enzyme preparation) at 37° C. for 90 minutes and the restriction enzyme inactivated by heating at 70° C. for 5 minutes. Poly-deoxyC sequences (for illustration purposes only depicted as CCC in FIG. 2) were attached to the 3′ termini of the digestion products by standard reaction with polynucleotide terminal transferase after removing the residual protein by extraction with phenol and chloroform (20 μl each). Phenol was removed from the aqueous phase by extraction with ether, and the DNA was precipitated by addition of 3M sodium acetate, pH 6.5 (5 μl) and cold ethanol 0.1 ml. After storage at −70° C. for one hour, the precipitated DNA was recovered by centrifugation at 10,000 r.p.m. for 20 minutes and the pellet dissolved in 10 mM tris-HCl pH 7.5 (10 μl). To this was added 3 μl of 400 mM potassium cacodylate, pH 7.0, 4 mM cobalt chloride, 4 mM deoxycytosine triphosphate (dCTP), 200 μg/ml bovine serum albumin and the mixture incubated at 27° C. for 10 minutes with 0.5 μl of polynucleotide terminal transferase (6000 u/ml) and the reaction stopped by addition of 50 mM EDTA (1 μl).

2. Preparation of Pst I Cleaved, dG-elongated pBR322

The plasmid pBR322 was digested with restriction endonuclease Pst I (for which the plasmid contains one target) and the products purified by phenol extraction and ethanol precipitation in the manner described above from HBV DNA. Poly-dG sequences (for illustration purposes only depicted as GGG in FIG. 2) were added to the 3′ termini of linear pBR322 molecules by terminal transferase as described for the addition of poly-dC sequences to HBV except that the reaction was carried out at 37° C.

3. Cohesion of G-elongated pBR322 and C-elongated HBV DNA

Equimolar amounts of the pBR322-poly-dG and HBV DNA-poly-dC were then mixed together and the complementary sequences allowed to link by incubation in 100 mM NaCl, 50 mM tris-HCl, pH 7.5, 5 mM EDTA (TNE), (50 μl) at 65° C. for one hour, followed by 47° C. for one hour, 37° C. for one hour and 20° C. for one hour and an equal volume of TNE and 20 μl of 100 mM $MgCl_2$, 100 mM $CaCl_2$, 100 mM tris-HCl, pH 7.5 was added.

4. Transformation of *E. coli* HB 101

Cultures of *E. coli* HB 101 competent for transformation were prepared as described by E. M. Lederberg and S. H. Cohen, "Transformation Of *Salmonella typhimurium* By Plasmid Deoxyribonucleic Acid", *J. Bacteriol.,* 119, pp. 1072–1074 (1974). 0.1 ml portions of the cells were mixed with 25 μl of the annealed DNA preparation and incubated at 0° C. for 20 minutes and then at 20° C. for 10 minutes before plating on L-agar plates containing tetracycline (50 μg/ml) for overnight incubation at 37° C. Since plasmid pBR322 includes the gene for tetracycline resistance, *E. coli* colonies which have been transformed with that plasmid will grow in cultures containing that antibiotic to the exclusion of those *E. coli* colonies not so transformed. Therefore, growth in tetracycline containing culture permits selection of properly transformed hosts.

5. Screening *E. coli* Colonies by Hybridization

Bacterial colonies grown on the incubated tetracycline containing L-agar plates were tested for sensitivity to ampicillin. The plasmid pBR322 includes the gene for ampicillin resistance. This gene is the proposed site of hybrid gene insertion. Therefore, colonies which have been transformed with a plasmid having DNA inserted at the chosen recognition site will be sensitive to ampicillin, but will retain their resistance to tetracycline. *E. coli* colonies that were sensitive to ampicillin but resistant to tetracycline were picked onto a disc of Millipore cellulose nitrate filter supported on L-agar plates containing tetracycline. After overnight growth at 37° C., the Millipore filter was transferred to fresh L-agar plates containing tetracycline and chloramphenicol (150 μg/ml) and incubated for a further several hours at 37° C. in order to amplify the number of copies of the plasmid within the cells (FIG. 2). The Millipore filters were then used for colony hybridization as described by M. Grunstein and D. S. Hogness, "Colony Hybridization: A Method For The Isolation Of Cloned DNAs That Contain A Specific Gene", *Proc. Natl. Acad. Sci. U.S.A.,* 72, pp. 3961–3965 (1975) with $^{32}P$-labelled HBV DNA prepared previously as the probe. Radioautography of the filters revealed the presence of colonies that contain DNA sequences complementary to authentic HBV DNA.

6. Detection of Colonies Synthesizing Polypeptides with HBV Antigenicity

Colonies that were resistant to tetracycline, sensitive to ampicillin and hybridized with authentic HBV DNA were tested for their ability to produce at least one polypeptide displaying HBV antigen specificity or antigenicity. Colonies were again picked onto Millipore filters supported on L-agar plates containing tetracycline and incubated at 37° C. overnight. A second plate of L-agar was covered with a culture of *E. coli* C600 (0.1 ml in 2 ml soft agar) infected with a virulent strain of bacteriophage λ vir (multiplicity of infection of about 1) and also incubated at 37° C. overnight by which time the bacterial lawn was confluently lysed (i.e. substantially all of the hosts' cell walls had burst) by the phage (λ vir). The Millipore filter containing cells transformed in accordance with this invention was lifted from its plate and placed, colonies downwards, in contact with the surface of the L-agar plate of *E. coli* C600 that had been lysed with λ vir. This contact was continued for about 10 minutes to permit infection of the cells residing on the Millipore filter by λ vir. The Millipore filter was then transferred to a fresh plate of L-agar and incubated at 37° C. for a further 5 hours. Meanwhile polyvinyl discs were coated with HBV antibodies as described by S. Broome and W. Gilbert, "Immunological Screening Method To Detect Specific Translation Products", *Prod. Natl. Acad. Sci. U.S.A.*, 75, pp. 2746–2749 (1978). The Millipore filter on which the transformed bacterial colonies were now obviously lysed were placed with the colonies in contact with the coated polyvinyl discs and kept at 4° C. for 3 hours. This contact results in any HBV antigens released from the lysed cells on the Millipore filter binding with the HBV antibodies of the disc. The coated discs were separated from the Millipore filter and then washed and incubated with $^{125}$I-labelled HBV antibodies. This incubation results in radioactive labelling of those sites on the disc where HBV antigens from the Millipore filter had previously been bound by the HBV antibodies of the disc. After washing and radioautography, as described by Broome and Gilbert, supra, colonies that had produced polypeptides with HBV antigen specificity were located by reference to the radioautograph.

USE OF POLYPEPTIDES AND GENES PRODUCED FROM RECOMBINANT DNA MOLECULES IN DETECTING THE PRESENCE OF HBV ANTIBODIES IN HUMANS

Polypeptides displaying HBV antigenicity and the structural genes and fragments which code therefor may be used in methods and kits designed to detect the presence of HBV antibodies in humans and therefore recognize humans and blood samples which have been infected by this virus.

For example, the HBcAg produced by hosts transformed by recombinant DNA molecules of this invention can be used in the immunological diagnostic tests currently available for hepatitis B virus detection, that is radioimmunoassay or ELISA (enzyme linked immunosorbent assay). In one type of radioimmunoassay anti-core antigen antibody, raised in a laboratory animal, is attached to a solid phase, for example, the inside of a test tube. HBcAg is then added to the tube so as to bind with the antibody. To the tube coated with the antigen-antibody complex is added a sample of the patient's serum, together with a known amount of HBV anti-core antibody labelled with a radioactive isotope such as radioactive iodine. Any HBV antibody in the patient's serum will compete with the labelled antibody for the free binding sites on antigen-antibody complex. Once the serum has been allowed to interact, the excess liquid is removed, the test tube washed, and the amount of radioactivity measured. A positive result, i.e. that the patient's serum contains HBV antibody, is indicated by a low radioactive count. In one type of ELISA test, a microtitre plate is coated with HBcAg and to this is added a sample of patient's serum. After a period of incubation permitting interaction of any antibody with the antigen, the plate is washed and a preparation of anti-human antibodies, raised in a laboratory animal, and which are linked to an enzyme label is added, incubated to allow reaction to take place, and the plate is then rewashed. Thereafter, enzyme substrate is added to the microtitre plate and incubated for a period of time to allow the enzyme to work on the substrate, and the adsorbance of the final preparation is measured. A large change in adsorbance indicates a positive result.

IN VIVO ACTIVITY OF POLYPEPTIDES PRODUCED FROM RECOMBINANT DNA MOLECULES

To test the biological activity of the antigenic polypeptides translated from the recombinant DNA molecule in the *E. coli* of this invention, sterile extracts of the bacterial cells which are shown to express HBcAg were injected into rabbits after mixing with an equal volume of Freund's adjuvant. Two animals received the crude bacterial extract and two were given samples of the same extract after fractionation on a Sephadex 650 column. Additional injections of the same sample, which have been frozen and stored (retaining full antigenic activity) were given two and five weeks after the first injection. The animals were bled at intervals several weeks after initial injection.

Immunodiffusion experiments, using the procedure described by O. Ouchterlony, "Immunodiffusion and Immunoelectrophoresis", in *Handbook of Experimental Immunology* (D. W. Weir ed.) (Blackwell Scientific Publications, Oxford and Edinburgh) chap. 19 (1967), were performed to compare the rabbit sera (antibodies) to human hepatitis B virus core antibody ("HBcAb") using HBcAg derived from human liver (B. J. Cohen and Y. E. Cossart, "Application Of A Screening Test For Antibody To Hepatitis B Core Antigen", *J. Clin. Path.*, 30, pp. 709–713 (1977)). All four rabbit sera gave precipitin lines with HBcAg identical to those formed between HBcAg and the HBcAb derived from human sources. Therefore, the core antigen synthesized in *E. coli* with the recombinant DNA molecules of this invention is serologically active in vivo. This activity establishes the feasibility of compositions and methods using viral antigens synthesized in microbial cells for the stimulation of antibody formation in humans. Such compositions and methods are characterized by the polypeptides produced in hosts transformed by recombinant DNA molecules prepared in accordance with this invention. These polypeptides would be employed alone or with well known pharmaceutically acceptable carriers such as saline solutions or other additives recognized by the art for use in compositions and methods for the treatment and prevention of viral infections in humans.

As noted previously, restriction enzymes other than the Kpn I/Pst I combination described above may be usefully employed in preparing recombinant DNA molecules of this invention. Other restriction sites in plasmid pBR322 and part of the HBV genome are depicted in FIGS. 2 and 3, respectively. In illustration of these alternative, but less preferred embodiments, the following examples are set forth.

BAM HI, ECO RI, BGL II—PST I COMBINATIONS

The HBV DNA fragments produced by the use of Bam HI Eco RI and Bgl II, unlike those produced by Kpn I, could not efficiently be directly tailed for cohesion owing to the presence of short 5' single-stranded projections. They were therefore treated with λ exonuclease to remove these projections before the addition of poly-dC sequences at 3' termini. This was done by incubation of the restricted DNA (10 μl of a solution as described earlier) with 15 μl 100 mM sodium glycinate, pH 9.5, 10 mM $MgCl_2$, 100 μg/ml bovine serum albumin, 5 μl λ exonuclease at 0° C. for 1.5 hours. The mixture was then extracted with phenol and chloroform and the process continued. In the preparation in which Bam HI was used, subsequent radioimmunoassay confirmed the production of polypeptides with HBV antigen specificity.

DIRECT LIGATION: ECO RI—ECO RI AND BAM HI—BAM HI

Instead of tailing the DNA fragments for cohesion, as described above, direct ligation of the gene fragments may be employed in the processes of this invention. For example, in two further preparations HBV DNA (20 ng) was restricted with restriction endonuclease Eco RI or Bam HI in 10 mM tris-HCl, pH 7.5, 10 mM $MgCl_2$, 10 mM 2-mercaptoethanol, 50 mM NaCl (10 μl) at 37° C. for 1.5 hours and mixed in excess with pBR322 that had been incubated with the same enzymes under identical conditions. A concentrated buffer solution (660 mM tris-HCl, pH 7.5, 100 mM $MgCl_2$, 10 mM EDTA, 100 mM 2-mercaptoethanol, 400 mM NaCl, 1 mM ATP) (2 μl) was added and the mixture incubated with T4 DNA ligase (0.5 μl) at 10° C. for 3 hours followed by 0° C. for at least 24 hours. The solution was diluted to 0.1 ml with 10 mM tris-HCl, pH 7.5 and used to transform competent cultures of E. coli HB 101 as described earlier. In the case of Bam HI prepared recombinant DNA molecules, the colonies were tested, before screening for hybridization, for sensitivity to tetracycline rather than to ampicillin, because the target for Bam HI in pBR322 is within the gene coding for tetracycline resistance and therefore successful insertion at this recognition site results in loss of this resistance instead of the ampicillin resistance as in the case of insertion at the Pst I site.

In the case of recombinant DNA molecules prepared via the Eco RI site, the colonies were tested, before screening for hybridization, for resistance to both ampicillin and tetracycline because the target for EcoRI in pBR322 is between the genes coding tetracycline and ampicillin resistance such that no inactivation of the genes for ampicillin or tetracycline resistance occurs on hybrid DNA insertion at this site.

Micro-organisms prepared by the processes described herein are exemplified by cultures deposited in the Culture Collection of the Microbiological Research Establishment at Porton Down on Dec. 15, 1978 and identified as pBR322-HBV-A to F.

Specifically, these cultures are characterized as follows:

A: E. coli HB 101/pBR322-Pst I dG:HBV-Kpn I dC: $Tet^R$ $Amp^S$ HBV+ VA+

B: E. coli HB 101/pBR322-Pst I dG:HBV-Bam HI dC: $Tet^R$ $Amp^S$ HBV+ VA+

C: E. coli HB 101/pBR322-Pst I dG:HBV-Bgl II dC: $Tet^R$ $Amp^S$ HBV+

D: E. coli HB 101/pBR322-Pst I dG:HBV-Eco RI dC: $Tet^R$ $Amp^S$ HBV+

E: E. coli HB 101/pBR322-Bam HI:HBV-Bam HI: $Tet^S$ $Amp^R$ HBV+

F: E. coli HB 101/pBR322-Eco RI:HBV-Eco RI: $Tet^R$ $Amp^R$ HBV+

Portions of these identical cultures have also been deposited in the Culture Collection of the National Collection of Industrial Bacteria, Aberdeen, Scotland on Dec. 20, 1979.

The above nomenclature for the cultures is a description of that culture as follows: Host/cloning vehicle—restriction site in cloning vehicle with indication of elongation nucleotide (if any): hepatitis B virus restriction site in hepatitis B virus with indication of elongation (if any): resistance (R) or sensitivity (S) to tetracycline (Tet) and ampicillin (Amp), positive hybridization to HBV DNA in the colony hybridization test, supra, (HBV+) and production of polypeptide displaying HBV antigenicity, supra, (VA+). Using this nomenclature culture pBR322-HBV-A designates an E. coli HB 101 culture containing as a plasmid a recombinant DNA molecule comprising pBR322 cleaved at the Pst I site and elongated with a poly dG tail at the 3' termini attached to HBV DNA cleaved with Kpn I and elongated with a poly-dC tail at the 3' termini, the culture displaying resistance to tetracycline, sensitivty to ampicillin, a positive HBV DNA hybridization test and producing a polypeptide displaying HBV antigenicity.

Of course, it is to be understood that the hybrid micro-organisms, recombinant DNA molecules and polypeptides and methods applicable to them of this invention are not limited to those described in the preferred embodiment above. Instead, the hybrid organisms, recombinant DNA molecules and polypeptides may be modified during production or subsequently by known methods to good advantage. For example, more efficient expression control sequences may be utilized for transcription of the HBV genes or hybrid genes, mutations to reduce the synthesis of undesired gene products may be introduced, the protease levels in the host cells may be reduced, thermo-inducible lysogens containing the HBV genes may be integrated into the host chromosome or other modifications and procedures may be carried out to increase the number of gene copies in the cell or to increase the cell's productivity in producing the desired polypeptides.

Apart from their use to produce polypeptides displaying HBV antigenicity, the hybrid micro-organisms of this invention are also useful for the production of large quantities of DNA containing all or part of the genome for hepatitis B virus. For example, amplification, e.g., by addition of chloramphenicol to the growth medium when the cell density has reached a suitable level, or the use of mutations to prevent lysis in bacteriophage hybrids that contain HBV sequences permit the preparation of HBV DNA in amounts previously unavailable.

HBV DNA prepared in this way may be used to determine the nucleotide sequence of the genome and from that the gene and amino acid sequences of the HBV antigens and structural genes themselves. Knowledge of these sequences aids in understanding the biology of the hepatitis B virus and permits the modifications described above to be employed to best advantage.

DNA FRAGMENT MAPPING AND NUCLEOTIDE SEQUENCE DETERMINATION

1. Hepatitis B Core Antigen

A series of recombinant DNA molecules, made in accordance with the processes described above, which imparted to their host cells the ability to synthesize HBcAg as detected by solid phase radioimmunoassay were chosen for sequence analysis. Fragments were prepared from these recombinant DNA molecules by digestion with appropriate restriction enzymes and the fragments labelled at their 5' termini with [$\alpha$-$^{32}$P] ATP and T4 polynucleotide kinase. The nucleotide sequences of each fragment were then determined by well-known chemical degradative methods (A. M. Maxam and W. Gilbert, "A New Method For Sequencing DNA", Proc. Nat. Acad. Sci. U.S.A., 74, pp. 560-564 (1977). The resulting nucleotide sequence is depicted in FIGS. 3-9. For reference, the sequence is numbered from the A of the ATG translational initiation codon of the core gene. The nucleotide sequence of the gene for HBcAg and the amino acid sequence for the polypeptide deduced from this gene (Reading Frame 1) is depicted in FIGS. 3-9 between nucleotides 1-549. The size of the polypeptide encoded by this gene is close to the 19000 molecular weight observed for core antigens from Dane particles. However, the present structural determination does not exclude the possibility that some amino acids may be trimmed from the amino terminus of this polypeptide in vivo during formation of the authentic antigen. This structure also does not take into account any other or further modifications to the polypeptide caused by its interaction with other human enzymes, e.g., those enzymes which glycosolate proteins. Therefore, the polypeptide structure determined herein may not be identical to that HBcAg found in vivo, but it will still elicit a very similar, if not identical, immuno response.

All of the recombinant DNA molecules examined had the HBV DNA inserted so that the core antigen gene was maintained in the same translational phase as the gene for penicillin resistance of pBR322. Moreover, in the various recombinants the HBV DNA insert began within one or two nucleotides of the same position in the HBV sequence. Because these recombinant DNA molecules originated from HBV DNA digested with various restriction enzymes, e.g., Bam HI and Kpn I, this unique attachment is surprising and may have resulted from inadvertent breakage or polynucleotide tailing of the HBV DNA at the nick in the endogenous DNA of the Dane particle (FIG. 1). Recombinant DNA molecules having the HBV DNA insert in a different translational phase did not express the HBcAg gene and no polypeptide displaying HBV antigenicity was detected in hosts transformed with such recombinant DNA molecules. Of course, it is to be understood that such non-gene expressing hosts and recombinant DNA molecules are still useful for producing HBV DNA in accordance with this invention.

While it was expected that HBcAg or fragments thereof produced through expression of the HBV DNA inserts would be fused to the product ($\beta$-lactamase) of the gene for penicillinase resistance via a small number of glycine residues, that was not the case. Instead, the $\beta$-lactamase was in each case fused through 5-8 glycines to an identical peptide sequence, but this sequence terminated after 25 amino acids. In this reading frame (Frame 1, FIG. 3), a stop codon (TAG) is followed three nucleotides later by an initiation codon from which translation continues unhindered to give a polypeptide 183 amino acids in length (FIGS. 3-8). Therefore, core antigenic activity resides in a polypeptide of about 21,000 daltons translated de novo from the HBV sequence within the mRNA transcribed from the recombinant DNA molecule. This polypeptide remains within the host cell because it is not attached to the excreted penicillinase carrier protein due to the arrangement of the stop and start codons of the HBV DNA insert.

2. Hepatitis B Surface Antigen

The nucleotide sequence of the gene for HBsAg and the amino acid sequence for the polypeptide deduced from this gene (Reading Frame 3) is also depicted in FIGS. 6-8, between nucleotides 1437-2114. The amino acid sequence of this polypeptide begins at the N terminus with the sequence met-glu-asn-ile-thr-ser. This initial amino acid sequence was determined by D. L. Peterson et al., "Partial Amino Acid Sequence Of Two Major Component Polypeptides Of Hepatitis B Surface Antigen", Proc. Natl. Acad. Sci. U.S.A., 74, pp. 1530-1534 (1977) from authentic human HBsAg. The amino acid sequence of this protein continues in FIGS. 6-8 to a stop codon 226 amino acids away. This 226 polypeptide sequence corresponds to a protein of 25,400 daltons.

The HBsAg length has been independently confirmed by sequencing appropriate recombinant DNA molecules by P. Valenzuela et al., "Nucleotide Sequence Of The Gene Coding For The Major Protein of Hepatitis B Virus Surface Antigen", Nature, 280, pp. 815-819 (1979) whose results showed several differences in both nucleotide and amino acid sequences from those in FIGS. 6-8.

The nucleotide sequence determined for the recombinant DNA molecules of this invention shows that none of those examined which expressed the gene for HBcAg can have the gene for HBsAg in a position from which it could also be expected to be expressed in an appropriate host cell. In fact, no HBsAg was detected in the extracts of cells transformed with those plasmids found to express the gene for HBcAg. However, as noted, supra, knowledge of the nucleotide sequences of these genes permits modification of the expression process to improve its yield and effect and to favor the expression of genes and the production of polypeptides not previously expressed or detected.

PREPARATION OF IMPROVED RECOMBINANT DNA MOLECULES FOR PRODUCTION OF HBV ANTIGENS

The gene and amino acid sequences of these antigens are useful in designing methods to increase the level of production of antigen or gene per bacterial cell.

The level of production of a protein is governed by two major factors: the number of copies of its gene within the cell and the efficiency with which these gene copies are transcribed and translated. Efficiency of transcription and translation (which together comprise expression) is in turn dependent upon nucleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to known expression control sequences so as to favor higher levels of expression. This having been achieved, the newly engineered DNA fragment may be inserted into a multicopy plasmid or a bacteriophage derivative in order to increase the number of gene copies within the cell and thereby further improve the yield of expressed protein.

Figure 10:
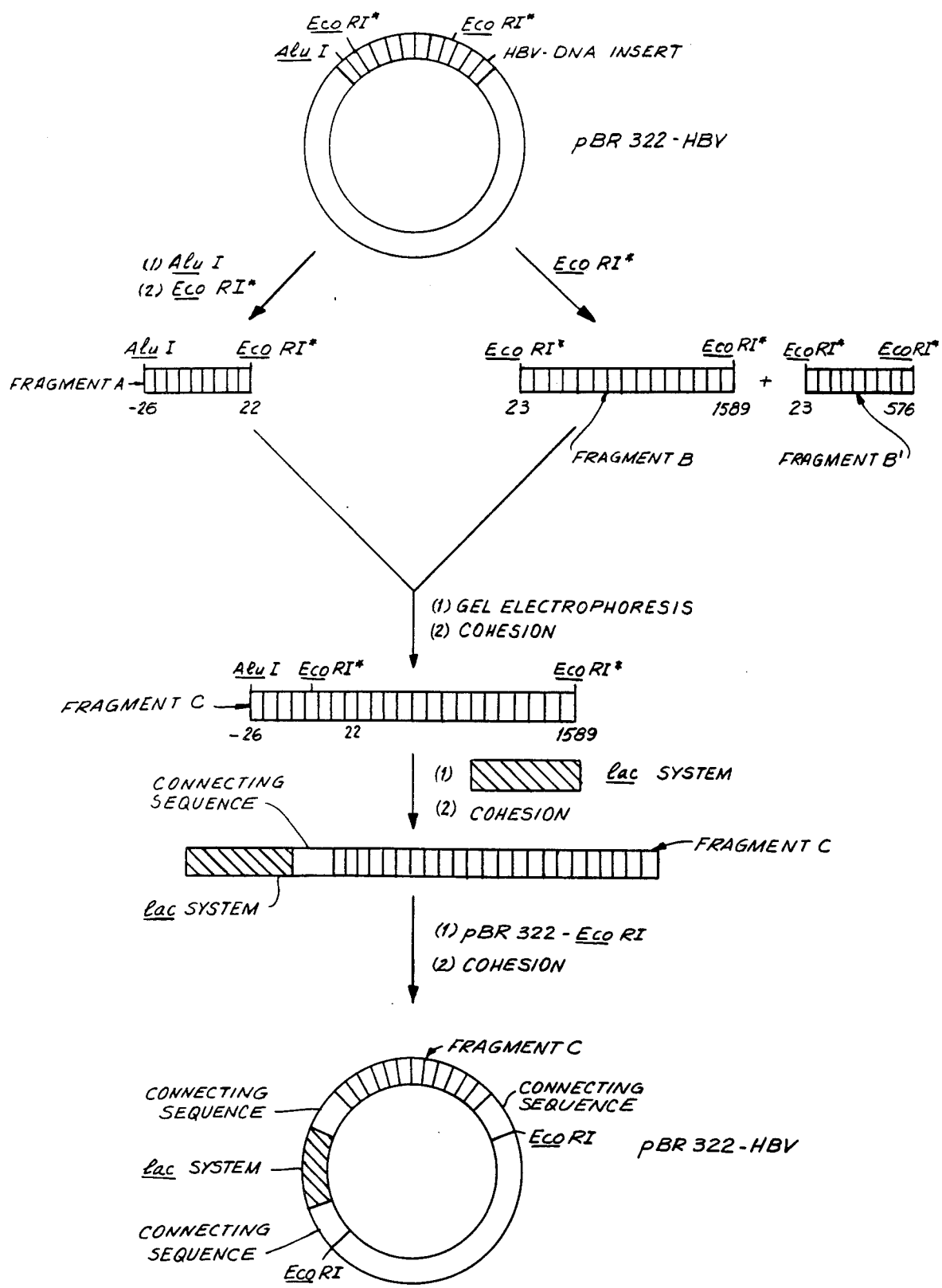
FIG. 10 is a schematic outline of a process of this invention wherein a recombinant DNA molecule which is capable of producing a polypeptide displaying hepatitis B virus core antigenicity is fragmented and a fragment therefrom attached to an improved expression control sequence, the lac system.

For illustrative purposes, the sequence determined for the gene of HBcAg has been employed in this way to improve the production of HBcAg in *E. coli*. One such process is depicted in FIG. 10.

Inspection of the DNA sequence for HBcAg in FIG. 3 reveals that this gene is preceded by a target for Alu I at nucleotide-26 (AGCT) and contains targets for Eco RI* at nucleotides 22 and 1590 (Raatty) for Eco RII at 209 (CCTGG), for Hae III at 280 (GGCC), and for Ava II at 246 and 461 (GGACC, GGTCC). Given this complexity, it is convenient to transfer a core antigen coding sequence to more efficient expression control sequences in two stages. For example, digestion of a recombinant DNA molecule (pHBV 114), prepared in accordance with this invention, having an HBV DNA insert of about 2350 base pairs (nucleotide pairs), i.e., from nucleotides −80 to about 2270 of FIG. 3, with both Alu I and Eco RI* gives, inter alia, the fragment between nucleotides −26 and 22 (Fragment A) while Eco RI* digestion alone gives the fragment from nucleotides 23 to 1589 (Fragment B) and low yields of a fragment from nucleotides 23 to 576 (Fragment B'). These fragments may be readily identified by reference to FIGS. 3–4 and are depicted schematically in FIG. 10. Fragments A and B are fractionated (e.g., by gel electrophoresis) to purify them and joined via their Eco RI* cohesive ends to give a combined fragment (Fragment C). Fragment C is now attached to a new expression control sequence as appropriate via direct ligation to maintain the correct translational phase, via the 3' tailing method described previously, or via synthetic oligo-nucleotide linkers. This attachment not only makes use of a better expression control sequence to improve protein production but it also permits the gene fragment coding for HBcAg to be attached closer to the expression control sequence itself so as to enhance control of that gene fragment's expression. In like fashion, Fragments A and B' may be joined or numerous other fragments prepared and the resultant fragment employed as above. This process demonstrates that only a portion of the structural gene coding for a particular polypeptide needs to be employed in the construction of recombinant DNA molecules of this invention.

To shorten even further the distance between the particular expression control sequence and the initiation codon of the chosen gene fragment, the particular fragment may be treated lightly with a combination of nucleases acting specifically at or near its terminus or used in exonuclease and polymerase-linked repair reactions to remove some or all of those nucleotides of the fragment preceding the fragment's start codon. Alternatively, a fragment, such as an Alu I fragment resulting from cleavage at nucleotides −26 and 30 could be similarly shortened with exonuclease treatment or polymerase-linked repair reactions and then cleaved with Eco RI* to produce a fragment from between nucleotides −26 and 1 and nucleotide 22 to permit fusion to fragment B before attachment to the expression control sequence. A further route might involve hybridization of fragment B, or an equivalent fragment, to an appropriate single stranded template from the parent recombinant DNA molecule for extension in a series of reactions with DNA polymerase and a limited number of nucleoside triphosphates so that the fragment strand could be reconstructed to the beginning of the coding sequence. The template strand would then be cleaved at the position of its association to the extended fragment strand with endonuclease S1 and the fragment so obtained attached to the expression control sequence.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phage λ ($O_L P_L$ and $O_R P_R^I$), and the control region of the phage fd coat protein. DNA fragments containing these sequences are excised by cleavage with restriction enzymes from the DNA isolated from transducing phages that carry the lac or trp operons, or from the DNA of phage λ or fd. These fragments are then manipulated in the manner outlined for the HBV antigen sequences in order to obtain a limited population of molecules such that the essential controlling sequences can be joined very close to, or in juxtaposition with, the initiation codon of the coding sequence for the desired antigen as described above for Fragment C.

The fusion product is then inserted as before into a cloning vehicle for transformation of the appropriate hosts and the level of antigen production measured by radioimmunoassay after lysis of the cells. Cells giving the most efficient expression may be thus selected. Alternatively, cloning vehicles carrying the lac, trp or λ $P_L$ control system attached to an initiation codon may be employed and fused to a fragment containing a sequence coding for a polypeptide displaying HBV antigenicity such that the structural gene fragment is correctly translated from the initiation codon of the cloning vehicle.

While these experiments have related to the production of HBV core antigen specifically, they are applicable to the improvement of the expression of other genes such as HBsAg and HBeAg genes and fragments thereof.

Further increases in the cellular yield of these particular antigens depend upon an increase in the number of genes that can be utilized in the cell. This has been achieved for illustration purposes by insertion of recombinant DNA molecules engineered in the way described previously into the temperate bacteriophage λ (NM989), most simply by digestion of the plasmid with a restriction enzyme, e.g., Eco RI or Hind III, to give a linear molecule which was then mixed with a restricted phage cloning vehicle (e.g., of the type described by N. E. Murray et al., "Lambdoid Phages That Simplify The Recovery Of In Vitro Recombinants", *Molec. gen. Genet.*, 150, pp. 53–61 (1977) and N. E. Murray et al., "Molecular Cloning Of The DNA Ligase Gene From Bacteriophage T4", *J. Mol. Biol.*, 132, pp. 493–505 (1979)) and the recombinant DNA molecule produced by incubation with DNA ligase. Such a procedure is depicted in FIG. 11. The desired recombinant phage was then selected by radioimmunoassay for the particular antigen or by hybridization with radioactively labelled HBV DNA sequences and used to lysogenise a host strain of *E. coli.*

Particularly useful λ cloning vehicles contain a temperature-sensitive mutation in the repressor gene cI and suppressible mutations in gene S, the product of which is necessary for lysis of the host cell, and gene E, the product of which is the major capsid protein of the virus. With this system the lysogenic cells are grown at 32° C. and then heated to 45° C. to induce excision of the prophage. Prolonged growth at 37° leads to high levels of production of the antigen, which is retained within the cells, since these are not lysed by phage gene products in the normal way, and since the recombinant phage genome is not encapsidated it remains available for transcription. Artificial lysis of the cells then releases the antigen in high yield (FIG. 11).

In addition to the *E. coli* systems with which these examples have been principally concerned, the same type of manipulations can be performed to increase the level of antigen production in other microbial cells, such a *B. subtilis,* thermophilic bacteria or yeasts and fungi, or in animal or plant cells in culture. In the case of *B. subtilis* a plasmid that carries the determinants for penicillinase isolated from *B. licheniformis* offers a useful expression control sequence for these purposes.

PREPARATION OF IMPROVED RECOMBINANT DNA MOLECULES FOR EXPRESSION OF THE GENE CODING FOR HBsAg

The gene and amino acid sequences determined for HBsAg are useful in designing methods to permit expression of the gene for HBsAg by the process of this invention. Such expression was not previously observed in hosts transformed with recombinant DNA molecules that produced polypeptides displaying HBV antigenicity.

The nucleotide sequence of FIGS. 6-8 displays the gene coding for HBsAg between nucleotides 1437 and 2114. This gene is in a different translational phase (Reading Frame 3) than the gene coding for HBcAg (Reading Frame 1) in the HBV genome of FIGS. 3-9. Therefore, a recombinant DNA molecule that did not produce HBcAg when used to transform an appropriate host, but contained an HBV DNA insert of about 2350 nucleotides (corresponding to about nucleotides −80 to 2270 of the sequence of FIGS. 3-8) was chosen for use in HBsAg production.

The selected recombinant DNA molecule contained, inter alia, the entire gene coding for HBsAg. Examination of the nucleotide sequence of the HBV DNA insert of this recombinant DNA molecule reveals several restriction endonuclease targets that permit excision of fragments containing the gene coding for HBsAg. E.g., nucleotide 1409 (Xho), nucleotide 1410 (Taq), nucleotide 1409 (Ava I) and nucleotide 1428 (Hha I) (FIG. 6). Of these the latter (Hha I) is particularly useful because cleavage of the HBV DNA insert occurs between nucleotides 1430 and 1431, a cut only six nucleotides in advance of the translational initiation codon (ATG) of the gene for HBsAg itself. In all four cases, the excised fragment will extend beyond the chosen HBV DNA insert to a target for the particular restriction endonuclease located within the nucleotide sequence of the pBR322 portion of the recombinant DNA molecule. Therefore, the use of these restriction endonucleases and others similarly useful, alone or in combination, permit the excision of the gene coding for HBsAg near but in advance of its initiation codon and after its translationa termination codon. Of course, is to be understood that as illustrated in the case of the gene for HBcAg, only fragments of the entire gene need be actually employed in recombinant DNA molecules to produce polypeptides displaying HBsAg antigenicity in appropriate hosts.

Fragments of HBV DNA derived from such digests have been treated in a series of reactions analogous to those described for the gene and gene fragments coding for core antigen. For example, the gene fragment may be inserted into the gene coding for penicillin resistance of pBR322 (e.g., Pst I recognition site, FIG. 2) producing the polypeptide displaying HBsAg antigenicity in fusion with β-lactamase (the product of the penicillinase gene), the gene fragment may be inserted between the genes coding for penicillin resistance and tetracycline resistance in pBR322 (Eco RI or Hind III recognition sites, FIG. 2) and joined there or before insertion to the lac system expression control sequence thereby producing the polypeptide displaying HBsAg antigenicity fused to the β-galactosidase protein of the lac system, the gene fragment may be inserted into a cloning vehicle as close as possible to the chosen expression control sequence itself as was described previously for the gene coding for HBcAg, or the gene fragment may be otherwise cloned as described in accordance with this invention.

For illustration purposes, one such scheme is depicted in FIG. 12. There, the selected recombinant DNA molecular having an HBV DNA insert (pHBV114) extending between about nucleotides −80 and 2270 (FIGS. 3-8) was fragmented by digestion with Ava I. The resulting fragment was inserted via the 3′ tailing method described previously at the Pst I site of pBR322. Hosts transformed with this recombinant DNA molecule produced polypepetides displaying HBsAg antigenicity.

Other fragments (e.g., Hha I, Taq, Xho, or Pst I (partial digest)) have also been inserted at the Pst I recognition site or other sites in pBR322 to produce recombinant DNA molecules which are useful for the production of polypeptides displaying HBsAg antigenicity or gene fragments coding for HBsAg.

In addition, such gene fragments have been inserted in pBR322 which had been cleaved by Pst I and the resulting fragment of the gene coding for penicillinase then digested away from the codon coding for amino acid 182 of penicillinase or β-lactamase in one case to the codon coding for amino acid 32 and in another case to the codon coding for amino acid 13 of that polypeptide. These derivative plasmids of pBR322-Pst I′ have also been employed with HBsAg gene fragments that extended from nucleotides 1447 to 1796 (FIGS. 6-7) to produce polypeptides displaying HBsAg antigenicity.

The nucleotide sequence between nucleotides 948 and 1437, immediately preceding the structural gene coding for HBsAg, may also be included in the fragments employed to produce useful recombinant DNA molecules for production of polypeptides displaying HBsAg antigenicity and gene fragments of the structural gene for HBsAg. This nucleotide sequence is referred to as the precursor sequence of the gene. Gene fragments including both this precursor sequence and the structural gene for HBsAg may be excised with Alu I (nucleotide 939), Hha I (nucleotide 900) or Hae II (nucleotide 899). In the case of Alu I and Hha I partial digestion and separation of the resulting fragments, e.g., by gel electrophoresis, is necessary because recognition sites for these enzymes also occur within the precursor sequence at nucleotide 1091 for Alu I and at nucleotide 1428 for Hha II.

Micro-organisms prepared by the processes described herein are exemplified by cultures deposited in the Culture Collection of the National Collection of Industrial Bacteria, Aberdeen, Scotland on Dec. 20, 1979 and identified as pBR322-HBV G-L and characterized as follows:

G: *E. coli* HB 101/pBR322-Pst I dG:HBV-Kpn I dC:(hereinafter "pHBV114"):$Tet^R$ $Amp^S$ HBV+

H: *E. coli* HB 101/pBR322-Pst I' dG:pHBV114-Pst I:$Tet^R$ $Amp^S$ HBV+ VA+

I: *E. coli* HB101/((pBR322-EcoRI, Baun HI:lac promoter sequence)-Hind III linkers: pHBV114-HhaI, Baun HI):$Tet^S$ $Amp^R$ HBV+ VA+

J: *E. coli* HB101/pUR2*-Eco RI:pHBV114-Hha I Eco RI linkers:$Tet^S$ $Amp^R$ HBV+ VA+

*A derivative of pBR322 having a DNA sequence including the gene coding replaced for the polypeptide for tetracycline resistance replaced with a smaller DNA sequence including the *E. coli* lac system.

K: *E. coli* HB 101/pBR322-Pst I dG-pHBV114-AVA I dC:$Tet^R$ $Amp^S$ HBV+ VA+

L: *E. coli* HB 101/pBR322-Pst I dG:pHBV114-Taq dC:$Tet^R$ $Amp^S$ HBV+ VA+

While we have hereinbefore represented a number of embodiments of this invention, it is apparent that our basic construction can be altered to provide other embodiments which utilize the process of this invention. Therefore, it will be appreciated that the scope of this invention is to be defined by the claims appended hereto rather than the specific embodiments which have been presented hereinbefore by way of example.

I claim:

1. A recombinant DNA molecule comprising an HBV DNA sequence, said HBV DNA sequence consisting essentially of a DNA sequence coding on expression in a unicellular host for a polypeptide displaying the antigenicity of an HBV core antigen or HBV surface antigen and being operatively linked to an expression control sequence in said DNA molecule.

2. The recombinant DNA molecule of claim 1, wherein the recombinant DNA molecule is a recombinant cloning vehicle comprising a first and a second restriction endonuclease recognition site, said HBV DNA sequence being inserted between said first and second restriction sites.

3. A unicellular host transformed with a recombinant DNA molecule, said molecule comprising an HBV DNA sequence, said HBV DNA sequence consisting essentially of a DNA sequence coding on expression in said unicellular host for a polypeptide displaying the antigenicity of an HBV core antigen or HBV surface antigen and being operatively linked to an expression control sequence in said DNA molecule.

4. The unicellular host of claim 3 wherein the recombinant DNA molecule is a recombinant cloning vehicle comprising a first and a second restriction endonuclease recognition site, said HBV DNA sequence being inserted between said first and second restriction sites.

5. A process for producing a recombinant DNA molecule comprising the steps of:
(a) preparing an HBV DNA sequence, the HBV DNA sequence consisting essentially of a DNA sequence coding on expression in a unicellular host for a polypeptide displaying the antigenicity of an HBV core antigen or HBV surface antigen;
(b) preparing a second DNA sequence, the second DNA sequence being capable of replication in an appropriate unicellular host and including an expression control sequence; and
(c) attaching the HBV DNA sequence to the second DNA sequence, said attachment operatively linking a DNA sequence coding on expression in a unicellular host for a polypeptide displaying the antigenicity of an HBV core antigen or HBV surface antigen of the HBV DNA sequence to the expression control sequence of the second DNA sequence.

6. The process for producing the recombinant DNA molecule of claim 5, wherein the second DNA sequence is prepared by cleaving a cloning vehicle with a restriction endonuclease and the HBV DNA sequence is attached to the cloning vehicle by insertion between the sites of cleavage therein.

7. A method for producing a polypeptide displaying the antigenicity of an HBV core antigen or HBV surface antigen comprising the steps of:
(a) preparing a recombinant DNA molecule, said molecule comprising (a) an HBV DNA sequence, said HBV DNA sequence consisting essentially of a DNA sequence coding on expression in a unicellular host for a polypeptide displaying the antigenicity of an HBV core antigen or HBV surface antigen and having operatively linked thereto an expression control sequence;
(b) transforming an appropriate unicellular host with said recombinant DNA molecule;
(c) culturing said host; and
(d) collecting said polypeptide.

8. The method of claim 7 wherein the recombinant DNA molecule is prepared by inserting the HBV DNA sequence between a first and second restriction endonuclease site of a cloning vehicle.

9. The method of claim 7 wherein the HBV DNA sequence is selected from the group consisting of the endogenous DNA of a Dane particle, fragments thereof and synthetically prepared equivalents thereto.

10. The method of claim 7 including the step of increasing the number of copies of the recombinant DNA molecule in the unicellular host.

11. The method of claim 7, wherein the HBV DNA sequence is prepared by a method comprising the steps of:
(a) isolating a recombinant DNA molecule from a culture of a unicellular host transformed with a recombinant DNA molecule, said molecule comprising an HBV DNA sequence, said HBV DNA sequence consisting essentially of a DNA sequence coding on expression in a unicellular host for a polypeptide displaying the antigenicity of an HBV core antigen or HBV surface antigen and being operatively linked to an expression control sequence in said DNA molecule; and
(b) excising form said isolated recombinant DNA molecule an HBV DNA sequence consisting essentially of a DNA sequence coding on expression in a unicellular host for a polypeptide displaying the antigenicity of an HBV core antigen or HBV surface antigen.

12. A method for producing an HBV DNA sequence, said HBV DNA sequence consisting essentially of a DNA sequence coding on expression in a unicellular host for a polypeptide displaying the antigenicity of an HBV core antigen or HBV surface antigen comprising the steps of:
   (a) preparing a recombinant DNA molecule having an HBV DNA sequence, said HBV DNA sequence consisting essentially of a DNA sequence coding on expression in a unicellular host for a polypeptide displaying the antigenicity of an HBV core antigen or HBV surface antigen and being operatively linked to an expression control sequence in said DNA molecule;
   (b) transforming an appropriate unicellular host with said recombinant DNA molecule;
   (c) culturing said host;
   (d) isolating said recombinant DNA molecule; and
   (e) excising an HBV DNA sequence therefrom.

13. The method of claim 12 wherein said recombinant DNA molecule is prepared by inserting the HBV DNA sequence between a first and second restriction endonuclease site of a cloning vehicle.

14. The method of claim 13 wherein said HBV DNA sequence is excised from between a first and a second restriction endonuclease site of a recombinant DNA molecule isolated from said unicellular host.

15. The method of claim 7 wherein the unicellular host is selected from the group consisting of strains of $E.\ coli$, Pseudomonas, Bacillus, yeast, other fungi, and animal and plant cells in culture.

16. The recombinant DNA molecule of claim 2, selected from the group consisting of pBR322-Pst I dG:HBV-Kpn I dC and pBR322-Pst I dG:HBV-Bam HI dC.

17. A unicellular host selected from the group consisting of $E.\ coli$ HB 101/pBR322-Pst I dG/HBV-Kpn I dC:Tet$^R$Amp$^S$HBV+VA+ and $E.\ coli$ HB 101/pBR322-Pst I dG/HBV-Bam HI dC:Tet-$^R$Amp$^S$HBV+VA+.

18. A method for producing a polypeptide displaying the antigenicity of an HBV core antigen or HBV surface antigen comprising the steps of:
   (a) culturing a unicellular host transformed with a recombinant DNA molecule, said molecule comprising an HBV DNA sequence, said HBV DNA sequence consisting essentially of a DNA sequence coding on expression in a unicellular host for a polypeptide displaying the antigenicity of an HBV core antigen or HBV surface antigen and having operatively linked thereto an expression control sequence; and
   (b) collecting said polypeptide.

19. A recombinant DNA molecule comprising an HBV DNA sequence, said HBV DNA sequence consisting essentially of a DNA sequence coding on expression in a unicellular host for a polypeptide displaying the antigenicity of an HBV core antigen and being operatively linked to an expression control sequence in said DNA molecule.

20. The recombinant DNA molecule of claim 19 wherein the recombinant DNA molecule is a recombinant cloning vehicle comprising a first and a second restriction endonuclease recognition site, said HBV DNA sequence being inserted between said first and second restriction sites.

21. A unicellular host transformed with a recombinant DNA molecule, said molecule comprising an HBV DNA sequence, said HBA DNA sequence consisting essentially of a DNA sequence coding on expression in said unicellular host for a polypeptide displaying the antigenicity of an HBV core antigen and being operatively linked to an expression control sequence in said DNA molecule.

22. The unicellular host of claim 21 wherein the recombinant DNA molecule is a recombinant cloning vehicle comprising a first and a second restriction endonuclease recognition site, said HBV DNA sequence being inserted between said first and second restriction sites.

23. A process for producing a recombinant DNA molecule comprising the steps of:
   (a) preparing an HBA DNA sequence, the HBV DNA sequence consisting essentially of a DNA sequence coding on expression in a unicellular host for a polypeptide displaying the antigenicity of an HBV core antigen;
   (b) preparing a second DNA sequence, the second DNA sequence being capable of replication in an appropriation unicellular host and including an expression control sequence; and
   (c) attaching the HBV DNA sequence to the second DNA sequence, said attachment operatively linking a DNA sequence coding on expression in a unicellular host for a polypeptide displaying the antigenicity of an HBV core antigen of the HBA DNA sequence to the expression control sequence of the second DNA sequence.

24. The process for producing the recombinant DNA molecule of claim 40 wherein the second DNA sequence is prepared by cleaving a cloning vehicle with a restriction endonuclease and the HBV DNA sequence is attached to the cloning vehicle by insertion between the sites of cleavage therein.

25. A method for producing a polypeptide displaying the antigenicity of an HBA core antigen comprising the steps of:
   (a) preparing a recombinant DNA molecule, said molecule comprising an HBV DNA sequence, said HBA DNA sequence consisting essentially of a DNA sequence coding on expression in a unicellular host for a polypeptide displaying the antigenicity of an HBV core antigen and having operatively linked thereto an expression control sequence;
   (b) transforming an appropriate unicellular host with said recombinant DNA molecule;
   (c) culturing said host; and
   (d) collecting said polypeptide.

26. The method of claim 25 wherein the recombinant DNA molecule is prepared by inserting the HBV DNA sequence between a first and second restriction endonuclease site of a cloning vehicle.

27. The method of claim 25 wherein the HBV DNA sequence is selected from the group consisting of the endogenous DNA of a Dane particle, fragments thereof and synthetically prepared equivalents thereto.

28. The method of claim 25 including the step of increasing the number of copies of the recombinant DNA molecule in the unicellular host.

29. The method of claim 25 wherein the HBV DNA sequence is prepared by a method comprising the steps of:
   (a) isolating a recombinant DNA molecule from a culture of a unicellular host transformed with a recombinant DNA molecule, said molecule comprising an HBV DNA sequence, said HBV DNA sequence consisting essentially of a DNA sequence coding on expression in a unicellular host for a polypeptide displaying the antigenicity of an HBV core antigen and being operatively linked to an expression control sequence in said DNA molecule; and (b) excising from said isolated recombinant DNA molecule an HBV DNA sequence consisting essentially of a DNA sequence coding on expression in a unicellular host for a polypeptide displaying the antigenicity of an HBV core antigen.

30. A method for producing an HBV DNA sequence, said HBV DNA sequence consisting essentially for a DNA sequence coding on expression in a unicellular host for a polypeptide displaying the antigenicity of an HBV core antigen comprising the steps of:

(a) preparing a recombinant DNA molecule having an HBV DNA sequence, said HBV DNA sequence consisting essentially of a DNA sequence coding on expression in a unicellular host for a polypeptide displaying the antigenicity of an HBV core antigen and being operatively linked to an expression control sequence in said DNA molecule;

(b) transforming an appropriate unicellular host with said recombinant DNA molecule;

(c) culturing said host;

(d) isolating said recombinant DNA molecule; and (e) excising an HBV DNA sequence therefrom.

31. The nethod of claim 30 wherein said recombinant DNA molecule is prepared by inserting the HBV DNA sequence between a first and second restriction endonuclease site of a cloning vehicle.

32. The method of claim 31 wherein said HBV DNA sequence is excised from between a first and a second restriction endonuclease site of a recombinant DNA molecule isolated from said unicellular host.

33. The method of claim 25 wherein the unicellular host is selected from the group consisting of strains of *E.coli, Pseudomonas, Bacillus,* yeast, other fungi, and animal and plant cells in culture.

34. The recombinant DNA molecule of claim 20 selected from the group consisting of pBR322-Pst I dG:HBV-Kpn I dC and pBR322-Pst I dG:HBV-Bam HI dC.

35. A unicellular host selected from the group consisting of E. coli HB 101/pBR322-Pst I dG/HBV-Kpn I dC: $Tet^R Amp^S HBV^+ VA^+$ and *E. coli* HB 101/pBR322-Pst I dG/HBV-Bam HI dC: $Tet^R Amp^S HBV^+ VA^+$.

36. A method for producing a polypeptide displaying the anitgenicity of an HBV core antigen comprising the steps of:

(a) culturing a unicellular host transformed with a recombinant DNA molecule, said molecule comprising an HBV DNA sequence, said HBV DNA sequence consisting essentially of a DNA sequence coding on expression in a unicellular host for a polypeptide displaying the antigenicity of an HBV core antigen and having operatively linked thereto an expression control sequence; and (b) collecting said polypeptide.

* * * * *